United States Patent [19]

Zelman et al.

[11] Patent Number: 5,433,702
[45] Date of Patent: Jul. 18, 1995

[54] PHACO HANDPIECE PROVIDING FINGERTIP CONTROL OF ULTRASONIC ENERGY

[75] Inventors: Jerry Zelman, Miami, Fla.; Theodore S. Cribari, Jr., Los Gatos, Calif.

[73] Assignee: Opthalmocare, Inc., Los Gatos, Calif.

[21] Appl. No.: 106,786

[22] Filed: Aug. 16, 1993

Related U.S. Application Data

[63] Continuation of Ser. No. 698,203, May 10, 1991, abandoned, which is a continuation-in-part of Ser. No. 537,616, Jun. 14, 1990, abandoned.

[51] Int. Cl.$^6$ .............................................. A61B 17/20
[52] U.S. Cl. ...................................... 604/22; 604/27; 200/61.58 R; 200/61.85; 200/295
[58] Field of Search .............. 128/24 AA; 604/20, 22, 604/27; 200/295, 61.58 R, 61.85, 61.86; 174/117 A

[56] References Cited

U.S. PATENT DOCUMENTS

| | | | |
|---|---|---|---|
| 3,226,501 | 12/1965 | Seserman | 200/61.58 R |
| 3,463,990 | 8/1969 | Ross | 200/61.85 |
| 3,589,363 | 6/1971 | Banko et al. | 604/22 |
| 3,752,160 | 8/1973 | Billin | 200/61.85 |
| 3,959,883 | 6/1976 | Walls et al. | |
| 4,293,752 | 10/1981 | Koenig | 200/295 |
| 4,552,143 | 11/1985 | Lottick | 200/295 |

FOREIGN PATENT DOCUMENTS

| | | |
|---|---|---|
| 8700027 | 1/1987 | Japan. |
| 2142163 | 1/1985 | United Kingdom. |
| 733693 | 5/1980 | U.S.S.R. |
| 1090391 | 5/1984 | U.S.S.R. |
| 1377104 | 2/1988 | U.S.S.R. |
| 1477414 | 5/1989 | U.S.S.R. |

OTHER PUBLICATIONS

Interlink Electronics Product Brochures.
Photocopies of product marketed by Valleylab.

Primary Examiner—David M. Shay
Attorney, Agent, or Firm—Sterne, Kessler, Goldstein & Fox

[57] ABSTRACT

A handpiece for the phacoemulsification of cataract tissue is provided in accordance with the present invention. The handpiece can be operatively coupled to a phacoemulsification machine to supply the handpiece with irrigation fluid, aspiration suction and ultrasonic energy. The application of irrigation fluid and aspiration suction to the handpiece are preferably controlled with a foot pedal which is operatively coupled to the phacoemulsification machine. The application of ultrasonic energy to the handpiece is controlled by a button, slide tab, knob or the like which is preferably detachably mounted to the main body of the handpiece so that the application of ultrasonic energy can be manually controlled by the surgeon.

17 Claims, 3 Drawing Sheets

PHACO HANDPIECE PROVIDING FINGERTIP CONTROL OF ULTRASONIC ENERGY

This application is a continuation, of application Ser. No. 07/698,203, filed May 10, 1991, now abandoned, which is a continuation-in-part of Ser. No. 07/537,616, filed Jun. 14, 1990, now abandoned.

BACKGROUND OF THE INVENTION

1. Field of the Invention

The present invention relates to a phacoemulsification handpiece and, more particularly, to a handpiece which provides fingertip control of ultrasonic energy during a phacoemulsification procedure.

2. Description of the Related Art

The human eye is divided by a normally transparent lens into anterior and posterior chambers. The transparent lens focuses light onto the retina defined on the rear surface of the posterior chamber. The lens of the eye may become cloudy for any one of a variety of reasons. When this happens, sight is impaired and the cloudy lens material must be removed. The function of the lens is then performed with an intraocular lens (IOL) implant or by using thick glasses or contact lenses.

A number of techniques are now being used for removing the cloudy, cataractous lens material. In all these techniques, a surgical tool is inserted into the eye through an incision. The phacoemulsification technique is a recently developed technique which is being used with increasing frequency. With that technique, an incision is made in the eye and a probe is inserted into the eye and into contact with the cataract tissue. Irrigation and aspiration passages are each defined through the probe and the probe is operatively coupled to a source of ultrasonic energy. Ultrasonic energy is selectively applied to the probe to break up the cataract tissue in contact with the tip of the probe so that the cataract tissue can be aspirated together with irrigating liquid. More particularly, the probe is manipulated to engage the harder cataract tissue which is then held in place by the aspiration and phacoemulsified by moving a foot pedal to activate ultrasound energy. The intensity of the ultrasound energy which can be applied is typically preselected by the surgeon. Ultrasonic energy is delivered as long as the foot pedal is held in position and is sufficient for phacoemulsifying the particles of cataract material.

Some conventional foot switches utilized with phacoemulsification machines and handpieces have four positions. There is a completely off position, where the foot pedal is not depressed at all, and an irrigation position, actuated by partial depression of the foot pedal. A combination of irrigation and aspiration is effected by a further depression of the foot pedal. Finally, there is an irrigation, aspiration and phaco position. With such a system, a fixed aspiration level is provided and the application of ultrasonic energy is either linear, that is a certain percent of power depending upon the disposition of the foot pedal, or fixed, that is a certain percent of power which is preselected by the surgeon.

In other conventional systems, a foot pedal is provided wherein there is a zero, or everything off, position, a first position where an irrigation fluid is supplied to the surgical site and a second position for irrigation and aspiration. With that system, instead of a fixed aspiration level, aspiration is linear from zero to the maximum millimeters of mercury which can be applied through the particular handpiece. Main phaco switching is provided to the right of the aspiration/irrigation foot pedal and is actuated by moving the foot to the right.

A disadvantage of the foregoing conventional systems is that the foot is utilized to control all the functions of the handpiece, specifically irrigation, aspiration and phaco whether linear or fixed. Because the foot does not have the touch sensitivity or fast, controlled response possible with, for example, the human hand, particularly when shoes are worn, it is difficult for the surgeon using his foot to properly time the application of phaco as well as to sense the amount of phaco being provided, when a linear application of phaco is utilized. Therefore, it would be desirable to provide a system for controlling ultrasonic energy delivered to a phacoemulsification handpiece which does not require use the surgeon's foot and hence does not exhibit the inherent inaccuracy and lack of control of conventional systems.

SUMMARY OF THE INVENTION

It is object of the invention to provide a phacoemulsification handpiece wherein application of ultrasonic energy is advantageously controlled by the surgeon's hand rather than by his foot whereas control of the irrigation and aspiration functions are effected with a foot pedal.

In order to achieve the foregoing and other objects, in accordance with the present invention, a switch is provided on the main body of the phacoemulsification handpiece itself which can be selectively activated by the surgeon's finger, for example his index finger, so that the timing of ultrasonic energy application and the amount of ultrasonic energy applied can be easily sensed and controlled.

In accordance another aspect of the invention, in order to provide control of ultrasonic energy with the surgeon's finger(s) or hand rather than with his foot, the control device of the invention can be detachably coupled to the phaco handpiece or to a remote surface, such as the surgeon's finger. Thus, the ultrasonic energy control device can be provided in a location which is practical for a particular surgeon and/or for a particular procedure. Such a selectively detachable control unit could be but need not necessarily be disposable. Switch as used here in below, therefore, refers generically to a switch permanently and fixedly mounted to a phaco handpiece or to switch which may be detachably coupled to the phaco handpiece, to the surgeon's finger or another part of the surgeon's body or to a structure which is readily accessible to the surgeon. Further, switch as used herein, encompasses on-off type switches, control units which allow the linear increase and/or decrease of ultrasonic energy and control units providing for control in stepped increments.

Other objects, features and characteristics of the present invention, as well as the methods of operation and functions of the related elements of the structure, and the combination of parts and economies of manufacture, will become more apparent upon consideration of the following detailed description and the appended claims with reference to the accompanying drawings all of which form a part of this specification, wherein like reference numerals designate corresponding parts in the various figures.

DETAILED DESCRIPTION OF THE PRESENTLY PREFERRED EXEMPLARY EMBODIMENTS

Figure 1:
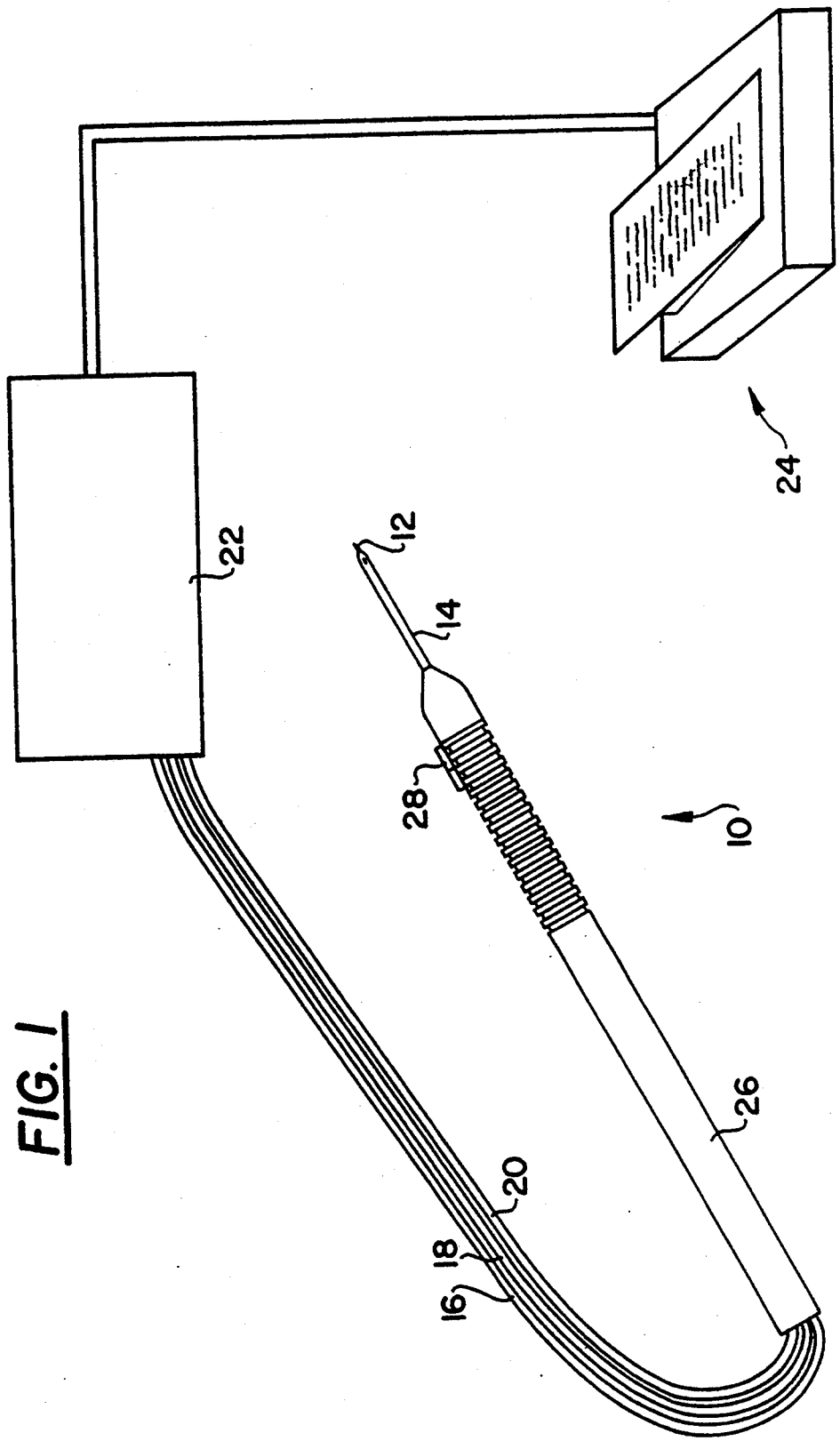
FIG. 1 is a schematic perspective view of a phacoemulsification apparatus, foot pedal and handpiece in accordance with the invention.

With reference to FIG. 1, the apparatus of the present invention includes a phaco handpiece 10 which may have, for example, a tubular probe 12 defining an aspiration passage and a sleeve 14 disposed thereabout and defining an irrigation passage for conveying irrigating fluid to a surgical site. At the proximal end of the phaco handpiece, means 16, 18 are provided for operatively coupling the aspiration passage and irrigation passage to a source of suction and a source of irrigating fluid, respectively. Further, means 20 are provided for operatively coupling the probe tip 12 of the handpiece 10 to a source of ultrasonic energy for selectively applying ultrasonic energy to the probe tip 12 to vibrate the same to emulsify cataract tissue in contact therewith.

A phacoemulsification machine shown generally at 22 is provided for allowing the surgeon to select a desired aspiration level or maximum and minimum aspiration levels for linear aspiration, as well as a desired power level or range of power levels for ultrasonic energy. Such determinations are made upon the age of the patient and the age of the cataract. Generally, a certain percentage of full power is designated as the desired maximum ultrasonic energy to be applied in a given procedure.

A foot pedal 24 is operatively coupled to phacoemulsification machine 22 in any known manner for controlling the irrigation and aspiration functions. Thus, depression of the foot pedal 24 by a certain amount will activate irrigation supply to the handpiece 10. Further depression of the foot pedal 24 will activate the aspiration function of the machine. Such aspiration activation can either be linear or fixed depending on the needs of the surgeon as determined prior to initiation of the surgical procedure. Where linear aspiration control is desired, depression of the foot pedal 24 will linearly increase the aspiration from a predetermined minimum to a predetermined maximum.

Figure 2:
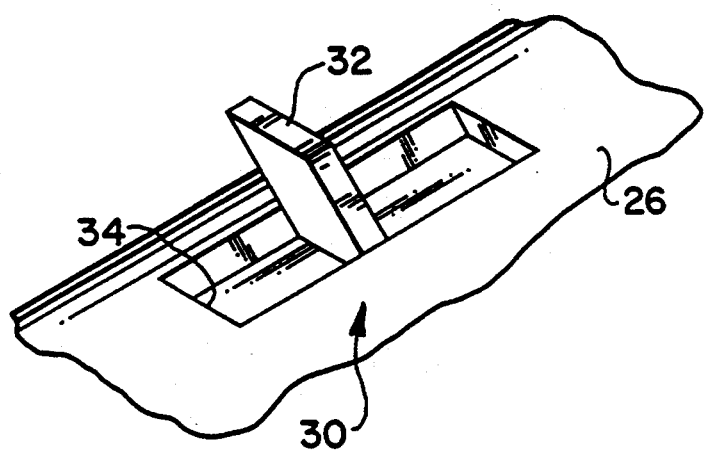
FIG. 2 is an enlarged perspective view of an alternate embodiment of a fingertip control device provided in accordance with the present invention.
Figure 3:
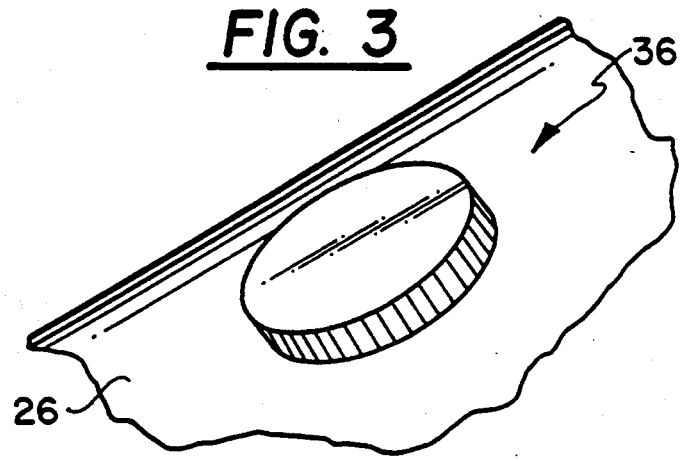
FIG. 3 is a perspective view of a further alternate fingertip control device in accordance with the invention.

In accordance with the present invention, control of the delivery of ultrasonic energy to the tip 12 of the handpiece 10 is controlled manually by the surgeon. Specifically, a switch for controlling the application of ultrasonic energy is defined on the main body 26 of the handpiece 10 and is accessible to the fingers of the surgeon, most preferably the surgeon's index finger. In the embodiment illustrated in FIG. 1, a button 28 is defined in the surface of the main body 26 handpiece 10. Such a system can be used, for example, to selectively turn on and turn off fixed application of phaco. With such a structure the surgeon would preselect a certain percentage of full phaco power at the phacoemulsification machine 22 prior to initiation of the procedure. Depression of the button 28 by the surgeon's index finger during the procedure, then, will apply the fixed phaco preselected by the surgeon to the probe tip 12 to allow emulsification of cataract tissue.

Where the linear application of phaco power is desired, a button 28 as shown in FIG. 1 can be provided which linearly increases the application of ultrasonic pressure with increased depression of the button 28. In the alternative, as shown in FIG. 2, a slide 30 can be provided in the handpiece so that movement of the upstanding tab 32 of the slide 30 relative to a longitudinal slot 34 in the main body 26 handpiece 10 will linearly increase or decrease the application of ultrasonic energy to the probe tip. As yet a further alternative, as shown in FIG. 3, a turn knob 36 can be provided on the main body 26 of the phaco handpiece which, like the slide 30, gradually increases or decreases ultrasonic energy to the probe tip 12.

As is apparent from the foregoing, any suitable switch, whether on and off or variable, can be provided on the main body or hand held portion of a handpiece in accordance with the present invention so as to provide fingertip control of the application of ultrasonic energy. The particular electrical and mechanical connections between the button, switch, knob or the like provided on the phaco handpiece and the phacoemulsification machine could be any suitable electro/mechanical system in which depression of a button, rotation of a knob or the like controls the delivery of power. Suitable systems are well known and would be readily apparent to the ordinary artisan upon review of this disclosure.

An on/off, a linear or a step switch in accordance with the present invention, as described hereinabove, can also be detachably coupled to the phaco handpiece so as to provide fingertip control of ultrasonic energy. Thus, for example, the switch for controlling ultrasonic energy may be in the form of a membrane switch 40 having a lead or leads 50, for example a positive lead and a negative lead for coupling the same to the ultrasonic energy control system. With such a structure, depressing the membrane switch 40 will effect contact closing the current flow path between the positive and negative leads and thereby actuate the application of ultrasonic energy.

The membrane switch 40 can be provided with an adhesive surface 42 which is covered prior to use with a non-stick backing 44. Thus, the membrane switch and attached leads could be provided as a disposable unit selectively electrically connected to the ultrasonic control center and applied to the handpiece so as to provide finger tip control as desired by the surgeon. More particularly, when the switch is to be attached to the handpiece, the non-stick backing 44 is peeled off to expose the adhesive surface 42 of the membrane switch 40 and the membrane switch 40 is applied to a desired portion of the phaco handpiece. In this manner, the membrane switch can be placed in the location which is most convenient to the surgeon and can accommodate the needs of either a right handed or left handed surgeon or a surgeon who utilizes a phaco handpiece handling technique which would otherwise render it difficult to access and operate a preformed, prelocated switch.

While a membrane switch has been described above, it is to be appreciated that any type of switch including a depressible button, a rotary knob or a slide could be suitably electrically coupled to the ultrasonic control system and coupled to the surface of the phaco handpiece so as to be selectively positioned, detached and/or discarded. For example, a potentiometer or the like could be mounted to the handpiece to provide variable control.

Further, while lead(s) 50 have been illustrated as providing communication between the switch and the primary ultrasound energy control, it is to be understood that other systems such as systems providing mechanical interconnection or a transmitter-type, wireless coupling between the switch and the ultrasound generating system could be provided without departing from the invention.

In accordance with yet a further aspect of the invention, rather than utilizing an adhesive backing for securing the switch to a desired location on the handpiece itself, the switch can be applied to a structure which is easily accessible to the surgeon such as, for example an arm rest, instrument support tray or the like. Even further, the switch could be coupled to the surgeon's finger. Pressing the surgeon's finger against the handpiece, then, would actuate ultrasonic energy application. Likewise, touching the finger to an adjacent, solid surface would effect the application of ultrasonic energy. Providing a switch which is attached to the surgeon's finger rather than to that handpiece itself provides the further significant and unobvious advantage that the handpiece can be rotated and moved without displacing the switch from ready access to the surgeon. Indeed, irrespective of the orientation of the handpiece or where along the handpiece's main body the surgeon's hand rests, ultrasonic energy can be positively and predeterminately controlled.

Figure 4:
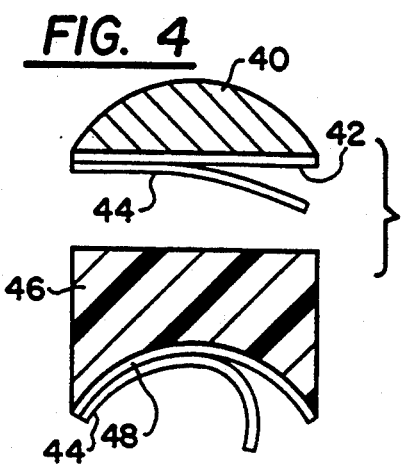
FIG. 4 is an elevational view of the switch adapter provided in accordance with the present invention.

In accordance with yet a further aspect of the invention, in order to avoid undesirable ultrasound actuation as a result of bending and curving the membrane switch in accordance with the shape of the handpiece surface, a switch mounting element or adapter 46 can be provided. As illustrated in FIG. 4, the adapter 46 is a plastic, stainless steel or hard rubber element which has a pressure sensitive adhesive 48 on a curved surface thereof which is exposed by peeling off a protective backing 44. The adapter is sized and the curved surface has a curvature designed to accommodate a particular manufacturer's phaco handpiece. Thus, the adapter can be provided in a variety of sizes and detailed shapes.

Figure 5:
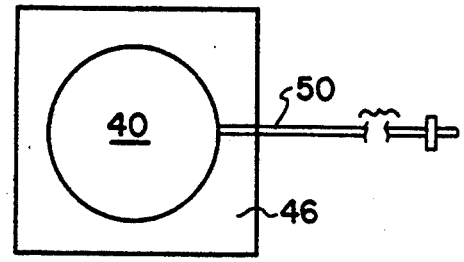
FIG. 5 is a top plan view of the adapter of FIG. 4.
Figure 8:
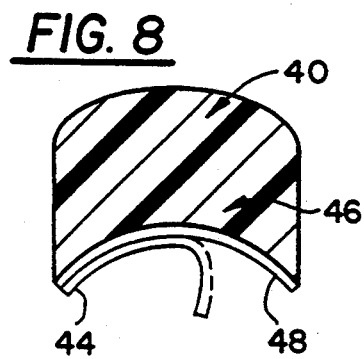
FIG. 8 is an elevational view of an integral adapter similar to FIG. 4.

The switch for controlling the ultrasonic energy in accordance with the invention is provided on a planer surface of the adapter. The switch may be in the form of a membrane switch which is permanently mounted to the planer surface of the adapter or integrally formed therewith (FIG. 8). In the alternative, the switch can be selectively attached to the adapter (as shown in FIGS. 4 and 5). The adapter 46 is autoclavable and reusable or may be provided as a disposable one use device.

Figure 6:
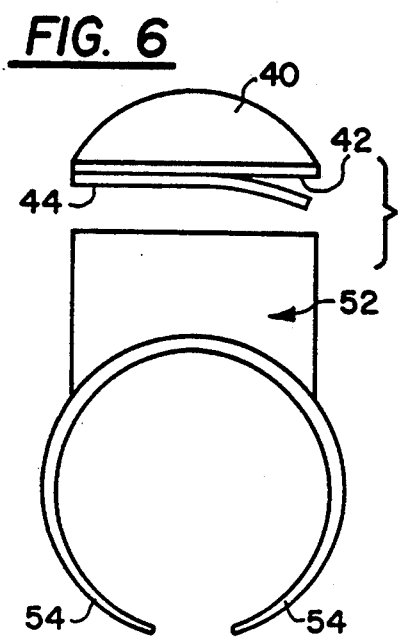
FIG. 6 is an elevational view of an alternate switch adapter provided in accordance with the present invention.
Figure 7:
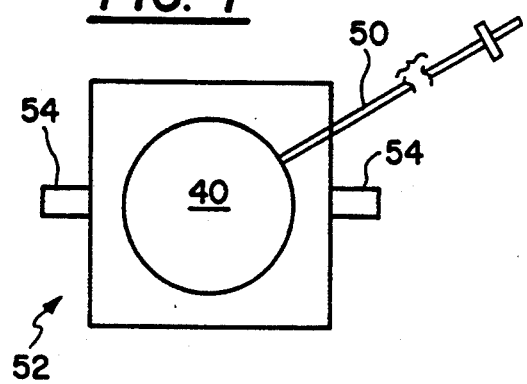
FIG. 7 is a top plan view of the switch adapter of FIG. 6.

As an alternative to adhesively securing an adapter to the handpiece as described above with reference to FIG. 4 and 5, the adapter may be in the form of a plastic, stainless steel or hard rubber ring 52 as illustrated in particular in FIG. 6. The ring has a planer surface for receiving a switch in accordance with the invention. For example, a disposable single use membrane switch 40 can be adhesively secured to the planer surface of the adapter ring 52. The ring, like the switch, can be disposable for single use or could be provided so as to be autoclavable and reusable. The ring can be slidably mounted to the phaco handpiece and thus, is preferably manufactured in a variety of sizes to accommodate the different diameters of various phaco handpieces which are being marketed. In that regard, the ring is preferably formed with two clamping fingers 54 to engage and grip the phaco handpiece. Indeed, providing a ring having an unstressed internal diameter slightly less than the diameter of the phaco handpiece will cause the clamping fingers 54 to be deflected outwardly slightly when the adapter ring is mounted to the handpiece so that the reaction force of the fingers tightly grips the surface of the handpiece and maintains the adapter in place once positioned.

As an alternative to slidably mounting the adapter ring to the phaco handpiece, the switch adapter ring 52 can be mounted to the surgeons's finger and the button activated by pressing it against another finger of the user or a hard surface such as the handpiece.

Figure 9:
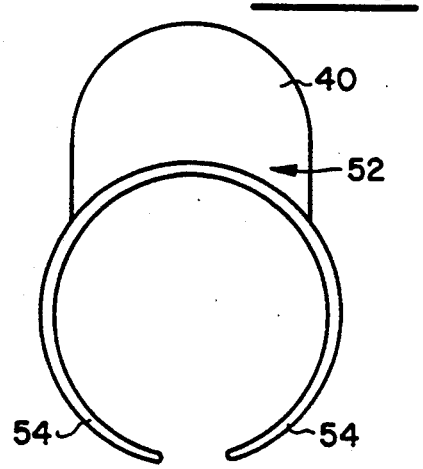
FIG. 9 is an elevational view of an integral adapter similar to FIG. 6.

While the switch provided on the adapter ring as illustrated in FIG. 6 is a membrane switch which is selectively attached to the adapter, it is to be understood that the switch may be permanently mounted on the planer surface of the adapter or integrally formed therewith (FIG. 9).

As is apparent from the foregoing, providing a switch which can be selectively coupled either with adhesive or with a clamp to either the surgeon's finger(s) or the phaco handpiece provides a structure which is uniquely versatile in that it can accommodate a particular surgeon's handling of the phaco handpiece or surgical style.

While the invention is described herein with reference to ophthalmic procedures and a phaco handpiece, it is to be understood that the detachable switch of the invention, in particular, can be advantageously used with other medical handpieces. Furthermore, the switch can be used to control functions other than ultrasound, such as aspiration, irrigation, laser energy, etc.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A handpiece having a fingertip control device comprising:
    a main body portion;
    a probe tip operatively coupled to said main body portion;
    a passage defined through said probe tip and through said main body portion;
    a means for respectively coupling said probe tip to a source of ultrasonic energy;
    an adapter having a planar surface, said adapter being disposed on said main body portion;
    a membrane switch disposed on said planar surface of said adapter for controlling delivery of energy to said probe tip so as to provide fingertip control of the same to said probe tip; and means for coupling said adapter to said main body portion at any position along a length and circumference of said main body portion whereby said switch can be selectively positioned on said main body portion.

2. A handpiece according to claim 1, wherein said membrane switch is adhesively disposed on said planar surface of said adapter.

3. A handpiece according to claim 1, wherein said membrane switch is permanently disposed on said planar surface of said adapter.

4. A handpiece according to claim 1, wherein said means for coupling said adapter to said main body portion comprises adhesive.

5. A handpiece according to claim 1, wherein said means for coupling said adapter to said main body portion comprises an adapter ring having clamping fingers.

6. A handpiece according to claim 1, wherein said passage defined through said probe tip and through said main body portion is coupled to a source of aspiration suction.

7. A handpiece according to claim 1, wherein said passage defined through said probe tip and through said main body portion is coupled to a source of irrigation fluid.

8. A handpiece comprising
a main body portion;
a probe tip disposed on said main body portion;
an aspiration passage defined through said probe tip and through said main body portion;
an irrigation passage defined through said probe tip and through said main body portion;
means for coupling said aspiration passage and said irrigation passage, respectively, to a source of aspiration suction and a source of irrigation fluid;
means for operatively coupling said probe tip to a source of energy;
an adapter having a planar surface, said adapter being disposed on said main body portion of said handpiece;
a membrane switch disposed on said planar surface of said adapter for controlling tile application of one of aspiration suction, irrigation fluid, and energy to said probe tip so as to provide fingertip control of the same to said probe tip; and
means for coupling said adapter to said main body portion at any position along a length and circumference of said main body portion whereby said membrane switch can be selectively positioned on said main body portion.

9. A handpiece according to claim 8, wherein said membrane switch is adhesively disposed oil said planar surface of said adapter.

10. A handpiece according to claim 8, wherein said membrane switch is permanently disposed on said planar surface of said adapter.

11. A handpiece according to claim 8, wherein said means for coupling said adapter to said main body portion comprises an adhesive.

12. A handpiece according to claim 8, wherein said means for coupling said adapter to said main body portion comprises an adapter ring having clamping fingers.

13. An apparatus for phacoemulsifying cataract tissue comprising:
a phacoemulsification machine having a source of irrigation fluid, a source of aspiration suction and a source of ultrasonic energy;
a handpiece including a main body portion;
a probe tip operatively coupled to said main body portion;
an aspiration passage defined through said probe tip and through said main body portion;
an irrigation passage defined through said probe tip and through said main body portion;
means for coupling said aspiration passage and said irrigation passage to said phacoemulsification machine;
means for operatively coupling said main body portion and said probe tip to said phacoemulsification machine;
an adapter having a planar surface, said adapter being disposed on said main body portion of said handpiece;
a membrane switch disposed on said planar surface of said adapter for controlling tile application of one of: aspiration suction, irrigation fluid, and ultrasonic energy to said probe tip so as to provide fingertip control of the same to said probe tip; and
means for coupling said adapter to said main body portion at any position along a length and circumference of said main body portion whereby said membrane switch can be selectively positioned on said main body portion.

14. An apparatus according to claim 13, wherein said membrane switch is adhesively disposed on said planar surface of said adapter.

15. An apparatus according to claim 13, wherein said membrane switch is permanently disposed on said planar surface of said adapter.

16. An apparatus according to claim 13, wherein said means for coupling said adapter to said main body portion comprises adhesive.

17. An apparatus according to claim 13, wherein said means for coupling said adapter to said main body portion comprises an adapter ring having clamping fingers.

* * * * *

UNITED STATES PATENT AND TRADEMARK OFFICE
CERTIFICATE OF CORRECTION

PATENT NO. : 5,433,702

DATED : July 18, 1995

INVENTOR(S) : Zelman et al.

It is certified that error appears in the above-identified patent and that said Letters Patent is hereby corrected as shown below:

Claim 8, column 7, line 26, after "comprising" insert --:--.
Claim 8, column 7, line 42, change "tile" to -- the--.
Claim 9, column 7, line 52, change "oil" to --on--.
Claim 13, column 8, line 32, change "tile" to --the--.
Claim 13, column 8, line 33, after "of" detete --:--.

Signed and Sealed this

Sixth Day of February, 1996

*Attest:*

BRUCE LEHMAN

*Attesting Officer*     Commissioner of Patents and Trademarks

UNITED STATES PATENT AND TRADEMARK OFFICE
CERTIFICATE OF CORRECTION

PATENT NO. : 5,433,702

DATED : July 18, 1995

INVENTOR(S) : Zelman et al.

It is certified that error appears in the above-identified patent and that said Letters Patent is hereby corrected as shown below:

On the Title Page, Item [73],
Assignee, please change "Opthalmocare, Inc." to --Ophthalmocare, Inc. --.

Signed and Sealed this

Fourteenth Day of May, 1996

*Attest:*

BRUCE LEHMAN

*Attesting Officer*     Commissioner of Patents and Trademarks